United States Patent [19]

Wakabayashi et al.

[11] Patent Number: 4,788,197

[45] Date of Patent: Nov. 29, 1988

[54] PYRAZINE DERIVATIVES USEFUL AS PLATELET AGGREGATION INHIBITORS

[75] Inventors: Toshio Wakabayashi, Tama; Hirokazu Hasegawa, Chofu; Akihiro Ohta, Tokyo, all of Japan

[73] Assignee: Terumo Kabushiki Kaisha, Tokyo, Japan

[21] Appl. No.: 170,692

[22] Filed: Mar. 14, 1988

Related U.S. Application Data

[63] Continuation of Ser. No. 844,103, Mar. 14, 1986, abandoned.

[30] Foreign Application Priority Data

Mar. 15, 1985 [JP] Japan .................................. 60-52115

[51] Int. Cl.[4] .................. A61K 31/495; C07D 241/12
[52] U.S. Cl. .................................... 514/255; 544/336; 544/410
[58] Field of Search .................. 544/336, 410; 514/255

[56] References Cited

U.S. PATENT DOCUMENTS 4,046,763  9/1977  Schwartz et al. .................... 544/410
4,064,124  12/1977  Weitz et al. .......................... 544/336

OTHER PUBLICATIONS

Beilsteins Handbook, of Organic Chemistry, 4th ed., vol. 23, p. 271 (1936).
Boyer, et al., Chem. Abstracts, vol. 78 (1973), Entry 124176s.
Chemical Abstracts, vol 83, No. 5, Aug. 4, 1975, Entry 43267y; Padwa, A., et al., "Synthesis of and Base-Induced Rearrangements in the 1,4-diazabicyclo[4.1.-0]-Hept-4-Ene System", J. Org. Chem., (1975) 40(12), pp. 1683-1688.
Chemical Abstracts, vol. 96, No. 9, Mar. 1, 1982, Entry 68932t; Yamanaka, H., et al., "Studies on Pyrimidine Derivatives, XXIII, Synthesis of Acylmethylpyrimidines and Related Compounds via Imidoylsubstituted Oxosulfonium Ylides", Chem. Pharm. Bull., (1981) 29(10), pp. 2837-2843.
Chemical Abstracts, vol. 102, No. 1, Jan. 7, 1985, Entry 6421j; Ohta, A., et al., "Introduction of the Methyl Group Into the Pyrazine Ring", Heterocycles (1984), 22(10), pp. 2317-2321.
J. Heterocyclic Chem., 21, 103 (1984).
Chemical Abstracts, vol. 99, No. 11, Sep. 12, 1983, Entry 88170h; Joshi, S. C., et al., "A New Synthesis of Pyrazines", Indian J. Chem., Sect. B (1983) 22B(4), pp. 396-397.

*Primary Examiner*—Donald G. Daus
*Assistant Examiner*—William A. Teoli, Jr.
*Attorney, Agent, or Firm*—Burns, Doane, Swecker & Mathis

[57] ABSTRACT

Novel pyrazine derivatives are disclosed. The compounds possess a potent platelet aggregation-inhibiting activity and are effective for preventing diseases caused by aggregation of the platelet, for example, myocardial infarction and cerebral thrombosis. Representative examples of the pyrazine derivatives includes 2,3-bis(p-chlorophenyl)-5-methylpyrazine, 2,3-bis(p-methoxyphenyl)-5-methylpyrazine, 2,3-diphenyl-5-benzylpyrazine, 2,3-diphenyl-5-(p-methoxybenzyl)pyrazine, 2,3-bis(p-methoxyphenyl)-5-isopropylpyrazine, 2,3-bis(p-methoxyphenyl)-5-(2-thienylmethyl)pyrazine and 2,3-bis(p-methoxyphenyl)-5,6-dimethylpyrazine.

The pyrazine derivatives can be generally prepared by heating a benzil derivative and a 1,2-diaminoethane derivative to produce a dihydropyrazine derivative and heating the resulting compound with sulfur at 100°–180° C.

6 Claims, No Drawings

PYRAZINE DERIVATIVES USEFUL AS PLATELET AGGREGATION INHIBITORS

This application is a continuation of application Ser. No. 844,103 filed Mar. 14, 1986, now abandoned.

BACKGROUND OF THE INVENTION

1. Field of the Invention

This invention relates to novel pyrazine derivatives. More particularly, it is concerned with pyrazine derivatives having the formula

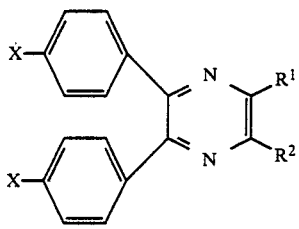

(I)

wherein X represents a hydrogen atom, a halogen atom, a lower alkyl group, a lower alkoxy group or a di-lower alkylamino group, $R^1$ represents a hydrogen atom or a lower alkyl group and $R^2$ represents a lower alkyl group, a benzyl group, a substituted benzyl group having as the substituent a lower alkyl group, a lower alkoxy group or a methylenedioxy group, a thienylmethyl group or a substituted thienylmethyl group having as the substituent a lower alkyl group, a lower alkoxy group or a methylenedioxy group.

The pyrazine derivatives (I) possess a potent platelet aggregation-inhibiting activity. Therefore, they are effective for preventing diseases caused by aggregation of the platelets, that is, such diseases as myocardial infarction and thrombosis. The pyrazine derivatives (I) of the invention also have a cycloxygenase-inhibiting activity. As compounds with such activity are generally known to possess an antiinflammatory activity, the pyrazine derivatives (I) are expected to find use as the antiinflammatory agent.

2. Description of the Prior Art

There have been known various compounds which have platelet aggregation-inhibiting activities. Their activities, however, are so weak that development of drugs possessing improved effects has been desired. There is also strong need for antithrombocytic agents which will effectively prevent thrombosis such as myocardial infarction and cerebral thrombosis, which recently occupy the major rate of adult diseases.

Heretofore, a variety of pyrazine derivatives are known, such as, for example, 2,3-diphenylpyrazine described in Journal of Heterocyclic Chemistry, vol. 21, pp. 103–106. However, none of these pyrazine derivatives are known to possess a platelet aggregation-inhibiting activity.

SUMMARY OF THE INVENTION

As a result of extensive studies on pharmacological activities of a variety of novel pyrazine derivatives prepared by us, we have found that specific pyrazine compounds possess a potent platelet aggregation-inhibiting activity and completed the present invention.

It is therefore an object of the invention to provide novel pyrazine derivatives which are useful as an antithrombocytic agent.

A further object of the invention is to provide antithrombocytic agent containing as the active ingredient such pyrazine derivatives.

DETAILED DESCRIPTION OF THE INVENTION

In accordance with the present invention there are provided novel pyrazine derivatives having the above-mentioned formula (I). In the above-mentioned formula (I), X represents a hydrogen atom, a halogen atom, for example, chlorine, bromine or fluorine atom, a lower alkyl group, for example, methyl, ethyl, propyl, isopropyl, butyl or isobutyl, a lower alkoxy group, for example, methoxy, ethoxy, propoxy, isopropoxy, butoxy or isobutoxy or a di-lower alkylamino group, for example, dimethylamino, diethylamino, methylethylamino, methylpropylamino, ethylpropylamino or dipropylamino; $R^1$ represents a hydrogen atom or a lower alkyl group, for example, methyl, ethyl, propyl, isopropyl or butyl; and $R^2$ represents a lower alkyl group, for example, methyl, ethyl, propyl, isopropyl, butyl or isobutyl, a benzyl group, a substituted benzyl group having as the substituent a lower alkyl group, a lower alkoxy group or a methylenedioxy group, for example, 3- or 4-methylbenzyl, 3- or 4-methoxybenzyl, 3- or 4-ethoxybenzyl, 3- or 4-propoxybenzyl or 3,4-methylenedioxybenzyl, a thienylmethyl group, for example, 2- or 3-thienylmethyl or a substituted thienylmethyl group having as the substituent a lower alkyl group, a lower alkoxy group or a methylenedioxy group, for example, 4- or 5-methyl-2- or 3-thienylmethyl.

As preferred examples of the pyrazine derivatives having the above-mentioned formula (I) are mentioned:
2,3-Diphenyl-5-methylpyrazine,
2,3-bis(p-chlorophenyl)-5-methylpyrazine,
2,3-bis(p-bromophenyl)-5-methylpyrazine,
2,3-bis(p-methylphenyl)-5-methylpyrazine,
2,3-bis(p-methoxyphenyl)-5-methylpyrazine,
2,3-bis(p-dimethylaminophenyl)-5-methylpyrazine,
2,3-bis(p-chlorophenyl)-5-ethylpyrazine,
2,3-diphenyl-5-benzylpyrazine,
2,3-diphenyl-5-(p-methylbenzyl)pyrazine,
2,3-diphenyl-5-(p-methoxybenzyl)pyrazine,
2,3-diphenyl-5-(m-methoxybenzyl)pyrazine,
2,3-bis(p-methoxyphenyl)-5-benzylpyrazine,
2,3-bis(p-chlorophenyl)-5-benzylpyrazine,
2,3-bis(p-methoxyphenyl)-5-isopropylpyrazine,
2,3-bis(p-methoxyphenyl)-5-ethylpyrazine,
2,3-bis(p-methoxyphenyl)-5-(2-thienylmethyl)pyrazine,
2,3-diphenyl-5-(2-thienylmethyl)pyrazine,
2,3-bis(p-chlorophenyl)-5-(2-thienylmethyl)pyrazine and
2,3-bis(p-chlorophenyl)-5-(4- or 5-methyl-2- or 3-thienylmethyl)pyrazine.

The pyrazine derivatives (I) are prepared by heating a benzyl derivative having the formula

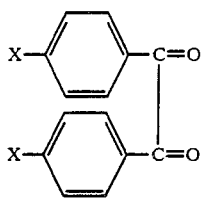

(II)

wherein X has the same meaning as described above and a 1,2-diaminoethane derivative having the formula

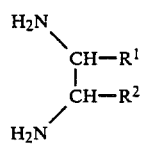

(III)

wherein $R^1$ and $R^2$ have the same meaning as described above in an appropriate organic solvent such as, for example, ethanol to produce a dihydropyrazine derivative having the formula

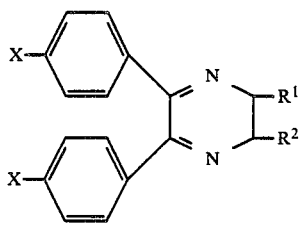

(IV)

wherein X, $R^1$ and $R^2$ have the same meaning as described above and subsequently heating the same with sulfur at 100°–180° C.

The pyrazine derivatives (I) wherein $R^1$ is a hydrogen atom and $R^2$ is a benzyl, substituted benzyl, thienymethyl or substituted benzyl group may also be prepared by reacting the above-described benzyl derivatives with 1,2-diaminoethane to produce a dihydropyrazine derivative and reacting the latter compound with a substituted or unsubstituted benzaldehyde or thiophenealdehyde. In the above preparative process, when a dialkyl ketone is reacted in place of the benzaldehyde the pyrazine derivatives (I) wherein $R^2$ is a branched chain-alkyl group can be produced. Furthermore, pyrazine derivatives of the above-described formula (I) wherein $R^1$ and $R^2$ are a lower alkyl group, respectively may also be obtained by oxidizing a 2,3-diphenylpyrazine derivative with permaleic acid to produce a mono- or di-N-oxide product, then chlorinating the same with phosphorus oxychloride to convert to a 2,3-diphenyl-4-(or 4,5)-chloropyrazine and reacting the same with a trialkylboron.

As the pyrazine derivatives (I) of the invention possess a platelet aggregation-inhibiting activity, they are effectively utilized as an antithrombocytic agent for prevention of cerebral thrombosis and like diseases. Moreover, the pyrazine derivatives (I) of the invention possess a cycloxygenase-inhibiting activity and are utilizable as an antiinflammatory agent.

The pyrazine derivatives of the invention may be administered at a dosage level in a range between about 30 and 600 mg per day in adults, if necessary, divided into one to three doses. The route of administration may be in any form suitable for administration, oral administration being particularly desirable with intravenous administration also feasible.

The compounds of the invention are formulated either alone or in admixture with pharmaceutical carriers or excipients by a conventional method into tablet, powder, capsule or granule. As examples of the carrier or excipient are mentioned calcium carbonate, starch, sucrose, lactose, talc, magnesium stearate and the like. In addition to the above-mentioned solid preparations, the compounds of the invention may also be formulated into liquid preparations such as oily suspension or syrup. They may also be stabilized in the form of inclusion in cyclodextrin.

The following examples and test examples are intended to illustrate the invention more concretely, but are not to be construed as limiting the scope thereof.

EXAMPLE 1

To a solution of 2.09 g of 4,4'-di-chlorobenzyl in 35 ml of ethanol was added dropwise 0.66 g of 1,2-propanediamine at room temperature. The mixture was heated under reflux for 30 minutes. The reaction mixture was concentrated to half of its original volume under reduced pressure. After ice-cooling, the produced precipitates were collected by filtration and recrystallized from ethanol to give 1.53 g of 2,3-bis(p-chlorophenyl)-5,6-dihydro-5-methylpyrazine as yellow needles with a melting point of 125°–126° C. 930 mg of the compound was mixed with 192 mg of powdery sulfur and the mixture was heated on an oil bath at 140° C. for 30 minutes. The reaction mixture was allowed to cool and subjected to column chromatography on silica gel. 630 mg of 2,3-bis(p-chlorophenyl)-5-methylpyrazine was obtained from the eluates with benzene. Physicochemical properties of the product support a chemical structure of the below formula (V).

M.P. 168°–169° C. (recrystallized from n-hexane).

Analysis:

Cal'd. for $C_{17}H_{12}N_2Cl_2$: C., 64.78%; H, 3.84%; N, 8.89%.

Found: C, 64.42%; H, 3.82%; N, 8.78%.

Mass (m/e): 314 (molecular ion peak).

$^1$H-NMR (CDCl$_3$) δ (ppm): 2.60(3H,s), 8.40 (1H,s). (ppm):

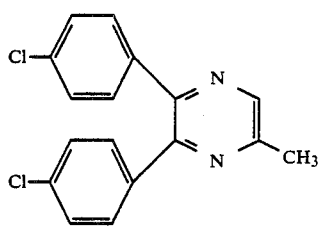

(V)

EXAMPLE 2

To a solution of 5.40 g of 4,4'-dimethoxybenzyl in 100 ml of ethanol was added dropwise 1.78 g of 1,2-propanediamine at room temperature. The mixture was heated under reflux for an hour. The reaction mixture was allowed to cool and insolubles precipitated were filtered off. The solvent was distilled off under reduced pressure from the mother liquor. The resulting residue was subjected to column chromatography on silica gel to obtain 3.549 g of 2,3-bis(p-methoxyphenyl)-5,6-dihydro-5-methylpyrazine from the eluate with a 1:1 n-hexane:methylene chloride mixture. To a solution of 1.004 g of the resulting product in 20 ml of methylene chloride was added 208 mg of powdery sulfur. The methylene chloride was distilled off under reduced pressure from the reaction mixture and the resulting residue was heated on an oil bath at 140° C. for 15 minutes. The reaction mixture was allowed to cool and subjected to column chromatography on silica gel to give 754 mg of 2,3-bis(p-methoxyphenyl)-5-methylpyrazine from the eluates with benzene. Physicochemical properties of the product support a chemical structure of the below formula (VI).

M.P. 120°–121° C. (recrystallized from methanol).
Analysis:
Calc'd. for $C_{19}H_{28}N_2O_2$:C, 74.49%; H, 5.92%; N, 9.14%.
Found: C, 74.63%; H, 6.20%; N, 9.12%.
Mass (m/e): 306 (molecular ion peak).
$^1$H-NMR (CDCl$_3$) δ(ppm): 2.60(3H,s), 3.77(3H,s), 6.77(2H,dd,J=2 Hz,10 Hz), 7.42(2H,dd,J=2 Hz,10 Hz), 8.40(1H,s).

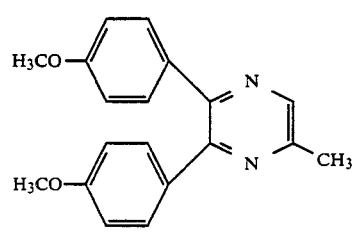

(VI)

EXAMPLE 3

In 20 ml of methanol were dissolved 2.570 g of 2,3-diphenyl-5,6-dihydropyrazine, 1.060 g of benzaldehyde and 0.672 g of potassium hydroxide. The solution was heated under reflux for 1 hour. Methanol was removed from the reaction solution by distillation under reduced pressure, and to the residue was added 50 ml of water. The resulting mixture was extracted three times with ethyl acetate. The organic layer from the extraction was washed with water and dried over anhydrous sodium sulfate. The solvent was removed by distillation under reduced pressure. The residue thus obtained was subjected to column chromatography on silica gel. A crude product was obtained from the eluates with an 8:1 hexane : ethyl acetate mixture. The crude product was recrystallized from hexane to give 2.940 g of 2,3-diphenyl-5-benzylpyrazine as colorless prisms. M.P. 118°–119° C. Physical properties of the product support a chemical structure of the below formula (VII).

Analysis: Calc'd. for $C_{23}H_{18}N_2$: C, 85.68%; H, 5.63%; N, 8.69%. Found: C, 85.68%; H, 5.53%; N, 8.67%.
Mass (m/e): 322 (molecular ion peak).
$^1$H-NMR (CDCl$_3$) δ(ppm): 4.27(2H,s), 8.47(1H,s).

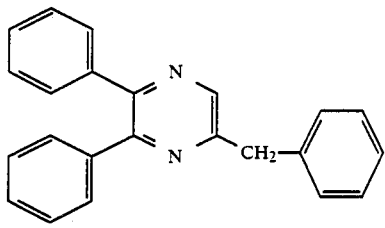

(VII)

EXAMPLE 4

The same procedures as in Example 3 were repeated using 2,3-diphenyl-5,6-dihydropyrazine and p-anisaldehyde. 2,3-Diphenyl-5-(p-methoxybenzyl)pyrazine was obtained as colorless prisms, m.p. 102°–103° C. (recrystallized from methanol-water). Physical properties of the product support a chemical structure of the below formula (VIII).

Analysis: Calc'd. for $C_{24}H_{20}N_2O$: C, 81.79%; H, 5 72%; N, 7.95%. Found: C, 81.89%; H, 5.70%; N, 8.01%.
Mass (m/e): 352 (molecular ion peak).
$^1$H-NMR (CDCl$_3$) δ(ppm): 73(3H,s), 4.17(2H,s), 6.83(2H,d,J=9 Hz), 8.37 (1H,s).

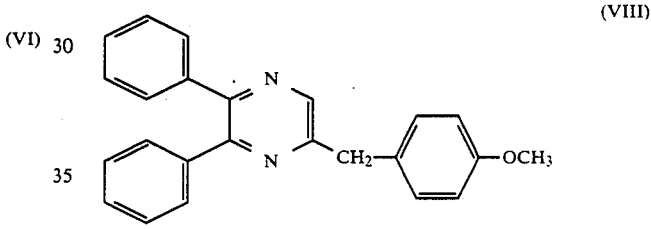

(VIII)

EXAMPLE 5

The same procedures as in Example 3 were repeated using 2,3-diphenyl-5,6-dihydropyrazine and m-anisaldehyde. 2,3-Diphenyl-5-(m-methoxybenzyl)pyrazine was obtained as colorless prisms, m.p. 65°–66° C. (recrystallized from methanol-water). Physical properties of the product support a chemical structure of the below formula (IX).

Analysis: Calc'd. for $C_{24}H_{20}N_2O$: C, 81.79%; H, 5.72%; N, 7.95%. Found: C, 82.02%; H, 5.74%; N, 7.97%.
Mass (m/e): 352 (molecular ion peak).
$^1$-NMR (CDCl$_3$) δ(ppm): 3.73(3H,s), 4.18(2H,s), 8.38(1H,s).

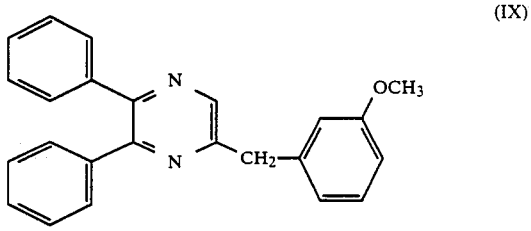

(IX)

EXAMPLE 6

The same procedures as in Example 3 were repeated using 2,3-bis(p-methoxyphenyl)-5,6-dihydropyrazine and benzaldehyde. 2,3-Bis(p-methoxyphenyl)-5-benzyl-pyrazine was obtained as colorless prisms, m.p. 107°–109° C. (recrystallized from methanol-water). Physical properties of the product support a chemical structure of the below formula (X).

Analysis: Calc'd. for $C_{25}H_{22}N_2O_2$: C, 78.51%; H, 5.80%; N, 7.33%. Found: C, 78.48%; H, 5.77%; N, 7.29%.

Mass (m/e): 382 (molecular ion peak).

$^1$H-NMR (CDCl$_3$) δ (ppm): 3.77(6H,s), 4.22(2H,s), 6.80(2H,d,J=9 Hz), 6.82 (2H,d,J=9 Hz), 8.33(1H,s).

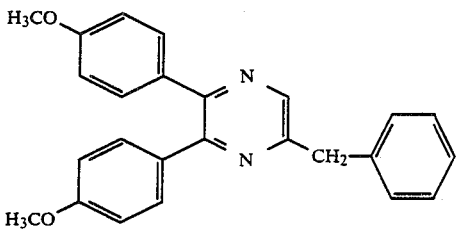

(X)

EXAMPLE 7

The same procedures as in Example 3 were repeated using 2,3-bis(p-methoxyphenyl)-5,6-dihydropyrazine and acetone. 2,3-Bis(p-methoxyphenyl)-5-isopropylpyrazine as an oily substance, b.p. 211° C. (0.15 Torr). Physical properties of the product support a chemical structure of the below formula (XI).

Analysis: Calc'd. for $C_{21}H_{22}N_2O_2$: C, 75.42%; H, 6.63%; N, 8.38%. Found: C, 76.19%; H, 6.76%; N, 8.48%.

Mass (m/e): 334 (molecular ion peak).

$^1$H-NMR (CDCl$_3$) δ (ppm): 1.37(6H,d,J=7 Hz), 3.75(6H,s), 6.78(4H,d,J=9 Hz), 7.35(2H, d,J=9 Hz), 7.41(2H,d,J=9 Hz), 8.37(1H,s).

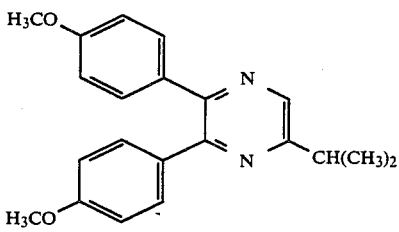

(XI)

EXAMPLE 8

To 20 ml of phosphorus oxychloride was added with stirring 3.918 g of 2,3-bis(p-methoxyphenyl)pyrazine oxide. The mixture was heated under reflux for 30 minutes. After allowed to cool, the reaction mixture was poured into ice water and then made basic with potassium carbonate to precipitate the product, which was collected by filtration. There was obtained 2.823 g of 2,3-bis(p-methoxyphenyl)-5-chloropyrazine. A mixture of 653 mg of said compound, 414 mg of anhydrous potassium carbonate and 116 mg of tetrakis(triphenylphosphine)palladium was suspended in an atmosphere of argon in 10 ml of dry N,N-dimethylformamide. To the suspension was added 2 ml of a hexane solution of triethylborane (15%). The resulting mixture was heated under reflux for 2 hours, followed by removal of the solvent by distillation under reduced pressure. Water was added to the residue, and the resulting mixture was extracted three times with methylene chloride. The organic layer from the extraction was washed with water and dried over anhydrous sodium sulfate. Removal of the solvent by distillation under reduced pressure afforded 850 mg of an extraction residue. The residue was subjected to column chromatography on silica gel. There was obtained 555 mg of 2,3-bis(p-methoxyphenyl)-5-ethylpyrazine from the eluates with a 1:1 hexane:methylene chloride mixture. M.P. 76.5°–78° C. (colorless needles, recrystallized from ethanol). Physical properties of the product support a chemical structure of the below formula (XII).

Analysis: Calc'd. for $C_{20}H_{20}N_2O_2$ C, 74.98%; H, 6.29%; N, 8.74%. Found: C, 75.02%; H, 6.41%; N, 8.73%.

Mass (m/e): 320 (molecular ion peak).

$^1$H-NMR (CDCl$_3$) δ (ppm): 1.37(3H,t,J=7 Hz), 2.87(2H, q,J=7 Hz), 3.77(6H,s), 6.77 (4H,d,J=7.5 Hz), 7.33(2H,d, J=7.5 Hz), 7.37(2H,d,J=7.5 Hz), 8.33(1H,s).

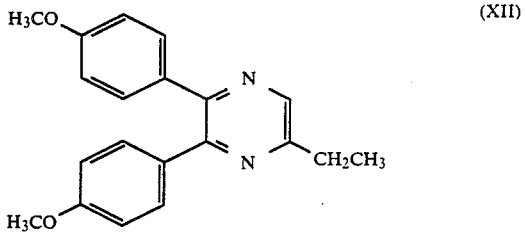

(XII)

EXAMPLE 9

The same procedures as in Example 3 was repeated using 2,3-bis(p-methoxyphenyl)-5,6-dihydropyrazine and 2-thiophenealdehyde. 2,3-Bis(p-methoxyphenyl)-5-(2-thienylmethyl)pyrazine was obtained as colorless prisms, m.p. 89° C. (recrystallized from methanol). Physical properties of the product support a chemical structure of the below formula (XIII).

Analysis: Calc'd. for $C_{23}H_{20}N_2O_2S$: C, 71.11%; H, 5.19%; N, 7.21%. Found: C, 71.19%; H, 5.25%; N, 7.22%.

Mass (m/e): 388 (molecular ion peak).

$^1$H-NMR (CDCl$_3$) δ (ppm): 3.77(6H,s), 4.40(2H,s), 6.80(2H,d,J=9 Hz); 6.92(2H, d,J=9 Hz), 7.37(2H,d,J=9 Hz), 7.43(2H,d,J=9 Hz), 8.40(1H,s).

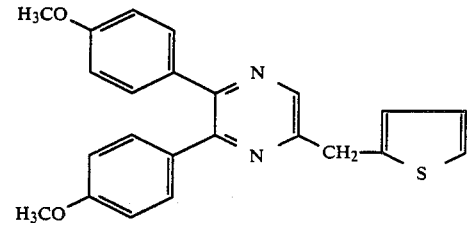

(XIII)

EXAMPLE 10

To 20 ml of phosphorus oxychloride was added with stirring 1,800 g of 2,3-bis(p-methoxyphenyl)pyrazine 1,4-dioxide. The mixture was heated under reflux for 1 hour. After allowed to cool, the reaction mixture was poured into ice water and made basic with potassium carbonate. The resulting mixture was extracted three times with methylene chloride. The organic layer from the extract was washed with water and dried over anhydrous sodium sulfate. The solvent was then removed by distillation under reduced pressure to obtain an extraction residue. The residue was subjected to column chromatography on silica gel to give 1.504 g of 2,3-bis(p-methoxyphenyl)-5,6-dichloropyrazine.

In 10 ml of dry tetrahydrofuran were dissolved in an atmosphere of argon 903 mg of said compound and 289 mg of tetrakis(triphenylphosphine)palladium. To the solution was further added 1.7 ml of a hexane solution of trimethylaluminum (15%). Then, the resulting mixture was heated under reflux for 4 hours. After allowed to cool, 1 ml of water was added to the reaction mixture, followed by removal of the solvent by distillation under reduced pressure. To the residue was again added 1 ml of water, and the mixture was extracted three times with methylene chloride. The organic layer from the extraction was washed with water and dried over anhydrous sodium sulfate. When the solvent was removed by distillation under reduced pressure, there was produced 1.30 g of an extraction residue. The residue was subjected to column chromatography on silica gel. There was obtained 694 mg of 2,3-bis(p-methoxyphenyl)-5,6-dimethylpyrazine from the eluates with methylene chloride. M.P. 106.5°–108° C. (colorless needles, recrystallized from ethanol). Physical properties of the product support a chemical structure of the below formula (XIV).

Analysis: Calc'd. for $C_{20}H_{20}N_2O_2$ C, 74.98%; H, 6.29%; N, 8.74%. Found: C, 74.89%; H, 6.25%; N, 8.90%.

Mass (m/e): 320 (molecular ion peak).

$^1$H-NMR (CDCl$_3$) δ (ppm): 2.57(6H,s), 3.77(6H,s), 6.78(4H,d,J=7.5 Hz), 7.37 (4H,d,J=7.5 Hz).

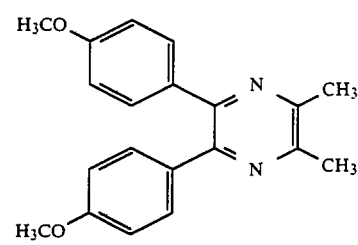

(XIV)

PHARMACOLOGICAL TEST EXAMPLE 1

Platelet Aggregation-Inhibiting Action

Nine volumes of blood was drawn from the carotid artery of a rabbit using a syringe containing one volume of 3.8% solution of sodium citrate. The blood was centrifuged to obtain platelet-rich plasma (PRP: $7 \times 10^5$ platelets/μl).

In a cuvette was placed 268 μl of the PRP, which was warmed in an isothermic bath at 37° C. for 2 minutes. To the cuvette was added 2 μl of an ethanol solution of a pyrazine derivative to be tested, followed by an incubation for 3 minutes. To the incubate was added a solution of a platelet-aggregation inducer, arachidonic acid or collagen. Measurement was made by Born's turbidimetric method (for example, see J. Physiol., vol. 168, p. 178, 1968). 50% inhibitory concentration for the platelet aggregation caused by arachidonic acid (50 μmol.) or collagen (10 μg/ml) was given in Table 1 using acetylsalicylic acid as the reference.

As shown in Table 1, the pyrazine derivatives of the invention were found to possess a marked platelet aggregation-inhibiting activity. The pyrazine derivatives not shown in Table 1 was also confirmed to possess a similar platelet aggregation-inhibiting activity. The 50% inhibitory concentration as shown in table means the concentration of a solution of the pyrazine derivative required for inhibiting the platelet aggregation to 50% when the platelet aggregation in the absence of a pyrazine derivative is taken as 100%.

TABLE 1

Platelet Aggregation Inhibiting Activity

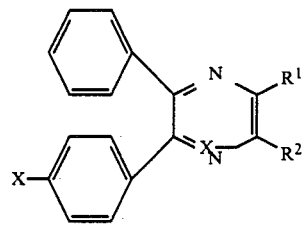

| Example No. | Substituent | | | 50% aggregation inhibitory concentration (mol.) | |
| --- | --- | --- | --- | --- | --- |
| | X | R$^1$ | R$^2$ | Arachidonic acid | Collagen |
| 1 | —Cl | H | —CH$_3$ | $8.5 \times 10^{-6}$ | $2.0 \times 10^{-5}$ |
| 2 | —OCH$_3$ | H | —CH$_3$ | $3.0 \times 10^{-8}$ | $4.2 \times 10^{-8}$ |
| 3 | H | H | —CH$_2$—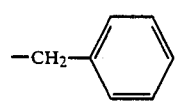 | $8.0 \times 10^{-6}$ | $4.6 \times 10^{-5}$ |

TABLE 1-continued
Platelet Aggregation Inhibiting Activity

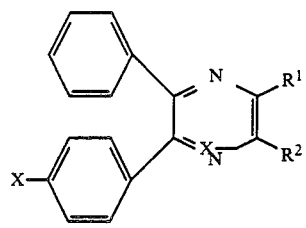

| Example No. | Substituent X | R¹ | R² | 50% aggregation inhibitory concentration (mol.) Arachidonic acid | Collagen |
|---|---|---|---|---|---|
| 4 | H | H | —CH₂—C₆H₄—OCH₃ | $1.7 \times 10^{-6}$ | $3.5 \times 10^{-5}$ |
| 5 | H | H | —CH₂—C₆H₄(OCH₃) | $4.5 \times 10^{-6}$ | $1.4 \times 10^{-5}$ |
| 6 | —OCH₃ | H | —CH₂—C₆H₅ | $2.0 \times 10^{-7}$ | $5.0 \times 10^{-6}$ |
| 7 | —OCH₃ | H | —CH(CH₃)₂ | $2.5 \times 10^{-8}$ | $7.9 \times 10^{-7}$ |
| 8 | —OCH₃ | H | —C₂H₅ | $4.6 \times 10^{-8}$ | $6.4 \times 10^{-7}$ |
| 9 | —OCH₃ | H | —CH₂-(2-thienyl) | $4.4 \times 10^{-7}$ | $7.9 \times 10^{-7}$ |
| 10 | —OCH₃ | —CH₃ | —CH₃ | $8.4 \times 10^{-8}$ | $9.2 \times 10^{-7}$ |
| Aspirin (Control) | — | — | — | $1.4 \times 10^{-5}$ | $5.6 \times 10^{-4}$ |

TEST EXAMPLE 2
Cycloxygenase Inhibiting Activity

Nine volumes of blood was drawn from the abdominal artery of a rabbit using a syringe containing one volume of 3.8% solution of sodium citrate. Centrifugation of the blood afforded platelet-rich plasma. To the platelet-rich plasma was added 77 mM EDTA solution in a volume of 1/10 per volume of the plasma. The mixture was thoroughly mixed and centrifuged at 2500 rpm for 10 minutes. The supernatant was discarded, and the platelets were suspended in approximately 3 ml of a washing solution which was prepared by dissolving 134 mM of sodium chloride, 15 mM of trisaminomethane, 1 mM of EDTA and 5 mM of D-glucose in twice-distilled water with a pH adjusted with 1N hydrogen chloride to 7.4. The suspension was centrifuged at room temperature at 2000 rpm for 10 minutes. The supernatant was discarded, and the precipitated platelets were re-suspended in a phosphate buffer at pH 8.0 to adjust number of the platelets to $1 \times 10^6$ per µl.

The washed platelets thus obtained were employed as a cycloxygenase source.

To 3 µg of arachidonic acid and 0.2 µCi (1 µg) of ¹⁴C-labelled arachidonic acid placed in a glass-stoppered test tube was added one drop of a propylene glycol/ethanol solution (1:3 by volume). The ethanol was evaporated under nitrogen. To the residue were added 50 µl of a solution to be tested and then 450 µl of the washed platelets. The mixture was reacted at 37° C. for 3 minutes.

To the reaction mixture was added with ice cooling one drop of 1N hydrogen chloride to adjust the pH to 2-3. To the resulting mixture was added 2 ml of ethyl acetate, followed by extraction by shaking for 10 minutes and centrifugal separation at 4° C. at 2500 rpm for 10 minutes.

The supernatant was transferred to a flask and concentrated. The residue was dissolved in 100 µl of ethanol, and the entire solution was spotted on a silica gel thin plate (Merck, 60 F₂₅₄).

The plate was developed by approximately 18 cm with a developer solution (chloroform/methanol/acetic acid/waters=70:8:1:0.8), followed by measurement by a radiochromatoscanner of the sum of radioactivities of prostaglandin F₂α, thromboxan B₂, prostaglandin E₂α, prostaglandin D₂ and HHT to determine the inhibiting activity. Results are shown in Table 2.

TABLE 2

| Example No. | Substituent X | R¹ | R² | 50% Inhibitory concentration (mol.) |
|---|---|---|---|---|
| 2 | —OCH₃ | H | —CH₃ | $3.0 \times 10^{-5}$ |
| 4 | H | H | —CH₂—C₆H₄—OCH₃ | $2.2 \times 10^{-4}$ |
| 9 | —OCH₃ | H | —CH₂-(2-thienyl) | $8.6 \times 10^{-5}$ |
| 10 | —OCH₃ | —CH₃ | —CH₃ | $6.2 \times 10^{-5}$ |

Acute Toxicity

An acute toxicity test was conducted in male ICR mice (5 week old) by oral administration. LD₅₀ values were 300 mg/Kg or higher for all of the pyrazine derivatives of the invention tested thereby demonstrating high safety.

What is claimed is:

1. A pyrazine compound having the formula

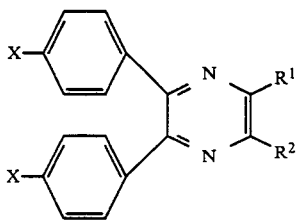

(I)

wherein X is independently selected from a hydrogen atom, a halogen atom, a lower alkyl group, a lower alkoxy group or a di-lower alkyl-amino group, R¹ represents a hydrogen atom or a lower alkyl group and R² represents a lower alkyl group; a benzyl group; a substituted benzyl group having as the substituent a lower alkyl group, a lower alkoxy group or a methylenedioxy group; a thienylmethyl group; or a substituted thienylmethyl group having as the substituent a lower alkyl group, a lower alkoxy group or a methylenedioxy group; with the proviso that if both X groups are a hydrogen atom and R¹ is a hydrogen atom, then R² cannot be methyl or ethyl; if both X groups are a hydrogen atom and R² is a hydrogen atom, then R¹ cannot be methyl or ethyl; and if both X groups are a hydrogen atom then R¹ and R² cannot both be methyl.

2. The pyrazine compound according to claim 1 wherein X is independently selected from a hydrogen atom, a halogen atom, a lower alkyl group or a lower alkoxy group, R¹ represents a hydrogen atom or a lower alkyl group and R² represents a lower alkyl group, a benzyl group, or a substituted benzyl group having as the substituent a lower alkoxy group.

3. A pharmaceutical composition of matter for use in inhibiting aggregation in a mammal, said composition comprising an effective amount of the pyrazine compound having the formula

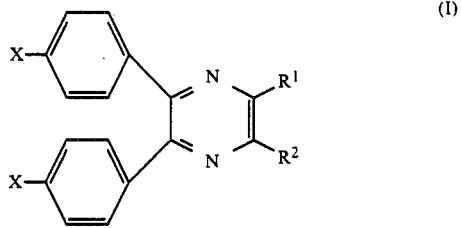

(I)

wherein X is independently selected from a hydrogen atom, a halogen atom, a lower alkyl group, a lower alkoxy group or a di-lower alkyl-amino group, R¹ represents a hydrogen atom or a lower alkyl group and R² represents a lower alkyl group; a benzyl group; a substituted benzyl group having as the substituent a lower alkyl group, a lower alkoxy group, a methylenedioxy group; a thienylmethyl group; or a substituted thienylmethyl group having as the substituent a lower alkyl group, a lower alkoxy group or a methylenedioxy group to inhibit platelet aggregation and a pharmaceutical carrier therefor.

4. A method for inhibiting the aggregation of platelets in a mammal, said method comprising administering to said mammal an effective amount of a pyrazine compound to inhibit aggregation of platelets, said pyrazine derivative having the formula

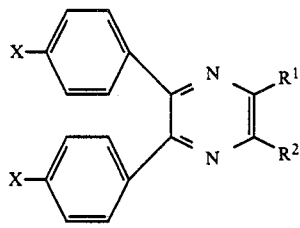

(I)

wherein X is independently selected from a hydrogen atom, a halogen atom, a lower alkyl group, a lower alkoxy group or a di-lower alkyl-amino group, R¹ represents a hydrogen atom or a lower alkyl group and R² represents a lower alkyl group; a benzyl group; a substituted benzyl group having as the substituent a lower alkyl group, a lower alkoxy group, a methylenedioxy group; a thienylmethyl group; or a substituted thienylmethyl group having as the substituent a lower alkyl group, a lower alkoxy group or a methylenedioxy group.

5. A method for treating a disease caused by aggregation of platelets in a mammal, said method comprising administering a therapeutically effective amount of the pyrazine compound to a mammal possibly afflicated with said disease, said pyrazine derivative having the formula

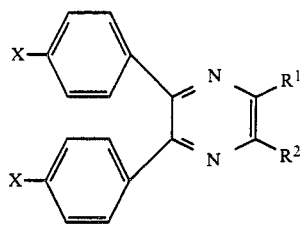

(I)

wherein X is independently selected from a hydrogen atom, a halogen atom, a lower alkyl group, a lower alkoxy group or a di-lower alkyl-amino group, $R^1$ represents a hydrogen atom or a lower alkyl group and $R^2$ represents a lower alkyl group; a benzyl group; a substituted benzyl group having as the substituent a lower alkyl group, a lower alkoxy group, a methylenedioxy group; a thienylmethyl group; or a substituted thienylmethyl group having as the substituent a lower alkyl group, a lower alkoxy group or a methylenedioxy group.

6. A method for treating a disease according to claim 5 wherein said disease is thrombosis.

* * * * *